(12) United States Patent
Edmundson et al.

(10) Patent No.: US 6,177,467 B1
(45) Date of Patent: Jan. 23, 2001

(54) USE OF N-L-α-ASPARTYL-L-PHENYLALANINE 1-METHYL ESTER AND ITS DERIVATIVES IN DISEASE REGRESSION

(75) Inventors: Allen B. Edmundson, Edmond; Carl V. Manion, Oklahoma City, both of OK (US)

(73) Assignee: Oklahoma Medical Research Foundation, Oklahoma City, OK (US)

( * ) Notice: Under 35 U.S.C. 154(b), the term of this patent shall be extended for 0 days.

(21) Appl. No.: 09/269,420

(22) PCT Filed: Sep. 26, 1997

(86) PCT No.: PCT/US97/17357

§ 371 Date: Mar. 26, 1999

§ 102(e) Date: Mar. 26, 1999

(87) PCT Pub. No.: WO98/13062

PCT Pub. Date: Apr. 2, 1998

Related U.S. Application Data

(60) Provisional application No. 60/026,720, filed on Sep. 26, 1996, and provisional application No. 60/044,831, filed on Apr. 25, 1997.

(51) Int. Cl.[7] .............. A61K 31/24; A61K 31/215; A61K 31/19
(52) U.S. Cl. ............ 514/538; 514/531; 514/575; 514/534
(58) Field of Search .................. 514/534, 531, 514/575, 538

(56) References Cited

U.S. PATENT DOCUMENTS

| | | | |
|---|---|---|---|
| 4,277,464 | 7/1981 | Reussner et al. | 424/177 |
| 4,752,602 | 6/1988 | Lipsky et al. | 514/19 |
| 5,654,334 | 8/1997 | Edmundson et al. | 514/538 |

FOREIGN PATENT DOCUMENTS

| | | |
|---|---|---|
| 2279250 | 1/1995 | (GB) . |
| 9221355 | 12/1992 | (WO) . |
| 9505166 | 2/1995 | (WO) . |
| 9514486 | 6/1995 | (WO) . |
| 9700692 | 1/1997 | (WO) . |

OTHER PUBLICATIONS

Mazur, Robert H; Schlatter, James M.; and Goldkamp, Arthur H., "Structure–Taste Relationships of Some Dipeptides", *Journal of the American Chemical Society*, 91:10, pp. 2684–2691 (1969).

Moreland, Larry W. et al., "Treatment of Rheumatoid Arthritis with A Recombinant Human Tumor Necrosis Factor Receptor (p75)–Fc Fusion Protein", *The New England Journal of Medicine*, vol. 337, No. 3, pp. 141–147 (1997).

Primary Examiner—Theodore J. Criares
(74) Attorney, Agent, or Firm—Sidley & Austin

(57) ABSTRACT

N-L-α-Aspartyl-L-phenylalanine 1-methyl ester (APM) and its derivatives have been found to effect disease regression in osteoarthritis, osteoporosis, and rheumatoid arthritis. APM performs as a TNF-α antagonist as well as an antipyretic agent.

28 Claims, 22 Drawing Sheets

USE OF N-L-α-ASPARTYL-L-PHENYLALANINE 1-METHYL ESTER AND ITS DERIVATIVES IN DISEASE REGRESSION

CROSS REFERENCE TO RELATED APPLICATIONS

This application claims the benefit of a 371 of PCT/US97/17357 filed Sep. 26, 1997, of prior filed copending U.S. Provisional Application No. 60/026,720 filed Sep. 26, 1996 and of prior filed copending U.S. Provisional Application No. 60/044,831 filed Apr. 25, 1997.

TECHNICAL FIELD OF THE INVENTION

The invention relates to a method for effecting disease regression, particularly various forms of arthritis.

BACKGROUND OF THE INVENTION

Bone functions as a supporting organ for the body and as a well organized dynamic system consisting of mineral, a matrix of collagen fibers, and cells. The cells include osteocytes, osteoblasts, and osteoclasts. The cells comprise 3–4% of the total volume. The collagen fibers are spatially oriented, highly organized into interlacing bundles and layers, and embedded in a gelatinous mucopolysaccharide ground substance which makes up 4–5% of the organic bone matrix. The mucopolysaccharides are covalently linked to noncollagenous proteins in combination with collagen to form a matrix of connective tissue. This protein matrix makes up 35% of the intercellular bone material, with minerals, mainly calcium, occupying the remainder.

Bone maturation is dependent upon activity of osteoblasts as well as certain bioelectrical fields in bone which are constantly produced by mechanical stress. The bioelectrical fields influence the spatial orientation of collagen fibrils and direct the structural development of the new bone as the bone material is mineralized.

Bone resorption is characterized by concomitant dissolution of both the bone matrix and mineral, and associated with osteoclasts and osteocytes. The method by which bone is dissolved is largely unknown. Collagenase, lysosomal proteases, and H+ are involved in solubilization of the mineral. The H+ is produced from organic acids and carbonic anhydrase derived from osteoclasts. Osteocytes are also involved in cortical bone resorption, releasing alkaline phosphatase, proteases, and lysosomal acid hydrolases. A variety of hormones and metabolic agents further control the balance between calcium and other minerals in bone and the circulating mineral pool.

Bone tissue is constantly undergoing remodeling and turnover via the slow process of bone formation and resorption. The amount of remodeling and turnover is age-dependent with rapid, 100% turnover in infants to slower 18% turnover in adults per year. Bone lability is maintained by concurrent, balanced activities of bone formation and resorption. Imbalances in the bone formation/resorption process lead to a variety of bone diseases.

Arthritis is a musculoskeletal disorder involving inflammation of the joints and its effects. Joint disease is one of the leading causes of activity limitations in the elderly. In its acute form, arthritis is marked by pain, inflammation, redness and swelling. There are three principle forms of arthritis: osteoarthritis, rheumatoid arthritis, and septic arthritis.

Osteoarthritis, also called osteoarthrosis or degenerative joint disease, is a disorder of the joints characterized by progressive deterioration of the articular cartilage. When the articular cartilage deteriorates by abrasion or wear, the bones change or shrink affecting the articular or hinge surfaces, causing further joint damage and pain. While the disease may be asymptomatic at early times, it later progresses to pain, stiffness, and limitation in movement. Common sites of discomfort are hips, knees, and vertebrae, i.e., joints that bear much of the weight of the body. The clinical manifestations of osteoarthritis and its subsequent treatment vary with the location and severity of the joint damage. Moderate symptoms are generally treated with combinations of any or all of analgesic and anti-inflammatory drugs, periodic rest, weight reduction, injection of corticosteroids, and physical therapy or exercise. More serious symptoms may be treated with invasive surgical procedures such as hip or knee replacement or joint debridement, i.e., removal of damaged tissue.

Rheumatoid arthritis is a chronic, progressive disorder in which the soft tissues of the joint become inflamed, irreversibly damaging joint cartilage and replacing it with deforming deposits of scar tissue. Rheumatoid usually affects joints of the body symmetrically such as both hands, feet, knees, hips, shoulders, and wrists. Serious incapacitation results in an estimated one-third of all cases. Rheumatoid arthritis is characterized by a gradual onset, beginning with pain and stiffness in one or more joints, usually followed by swelling and heat, muscle dysfunction and pain. Fatigue, muscle weakness, weight loss, and the presence of a characteristic autoantibody, i.e, rheumatoid factor, are also commonly present. Treatment for pain and disability include analgesics such as aspirin and ibuprofen which have anti-inflammatory properties. Small doses of corticosteroids such as prednisone may be prescribed when large doses of analgesics do not relieve pain and inflammation. Physical therapy is useful in relieving pain and swelling in the affected joints. Rest is also suggested during acute stages to prevent deformity. In severe cases, surgery may be used to replace destroyed hip, knee or finger joints.

Septic arthritis results from an infection in connective tissues generally caused by some form of invasive trauma. Pain and inflammation are associated with the infected tissue. Treatment generally involves use of antibiotic and/or antifungal agents as well as analgesic, anti-inflammatory, and antipyretic drugs for pain and inflammation.

The analgesic and anti-inflammatory drugs of choice for all three forms of arthritis are nonsteroidal anti-inflammatory drugs (NSAIDS) which provide relief from the pain and inflammation associated with arthritis. These drugs include salicylic acid derivatives such as aspirin; indole and indene acetic acids such as indomethacin, sulindac, and etodolac; heteroaryl acetic acids such as diclofenac; arylpropionic acids such as ibuprofen and naproxen; fenamates; and alkanones such as apazone. While these drugs show varying strengths in analgesic, anti-inflammatory, and antipyretic properties, they also have unwanted side effects. The most common is gastrointestinal side effects including gastric and/or intestinal ulceration, dyspepsia, and heartburn. Other side effects include disturbances in platelet function, the prolongation of gestation or spontaneous labor, and changes in renal function.

While providing relief from the symptoms of arthritis, these drugs do not arrest the progression of the course of the arthritic disorder. There is a need for drugs which will decrease joint damage as well as provide relief from the pain and inflammation associated with the disease process.

For rheumatoid arthritis, studies indicate that proinflammatory cytokines, particularly tumor necrosis factor (TNF), play a significant role in its pathogenesis, acting as an immune modulator in acute and chronic inflammation (Moreland, et al., "Treatment of rheumatoid arthritis with a recombinant human tumor necrosis factor receptor (p75)-Fc fusion protein," *New England J Med* 337:141–147 (1997); Arend, W. P. and Dayer, J. M., "Inhibition of the production and effects of interleukin-1 and tumor necrosis factor α in rheumatoid arthritis," *Arthritis Rheum* 38:151–160 (1995); Brennan, F. M. and Feldmann, M., "Cytokines in autoimmunity," *Curr Opin Immunol* 4:754–759 (1992)). Persons with active rheumatoid arthritis have an increased TNF concentration in the synovial fluid, and increased TNF plasma levels are associated with joint pain in rheumatoid arthritis patients. Administration of TNF antagonists to patients with rheumatoid arthritis has been shown to reduce symptoms (Elliott, et al., "Repeated therapy with monoclonal antibody to tumor necrosis factor α (cA2) in patients with rheumatoid arthritis," *Lancet* 344:1125–1127 (1994); Elliott, et al., "Randomized double-blind comparison of chimeric monoclonal antibody to tumor necrosis factor α (cA2) versus placebo in rheumatoid arthritis," *Lancet* 344:1105–1110 (1994); Elliott, et al., "Treatment of rheumatoid arthritis with chimeric monoclonal antibodies to tumor necrosis factor α," *Arthritis Rheum* 36:1681–1690 (1993); Rankin, et al., "The therapeutic effects of an engineered human anti-tumor necrosis factor alpha antibody (CDP571) in rheumatoid arthritis," *Br J Rheumatol* 34:334–342 (1995)). Therefore, it is desirable to identify new substances which are capable of acting as antagonists of proinflammatory cytokines such as TNF. Particularly, it is desirable to identify new substances capable of diminishing the deleterious effects of TNF-α in rheumatoid arthritis patients.

The normal supportive function of bone requires an adequate supply of amino acids for the synthesis of collagen as well as calcium and phosphate for mineralization. The growth, repair and remodeling of bone tissue also require a precisely regulated supply of hormones, vitamins, and enzymes. Skeletal disease or abnormality caused by inadequacies in the supply or action of these essential elements is termed metabolic bone disease. Osteoporosis is one example of metabolic bone disease.

Osteoporosis is a condition of low bone tissue mass per unit volume and skeletal weakness that results in fractures with minimal trauma. Characteristic sites of fracture include the neck, humerus, tibia, wrist, and pelvis. Bone resorption is increased, and while bone formation appears to be normal, there may be a decrease in the quality of bone tissue formed. Osteoporosis is generally described as primary or secondary. Secondary osteoporosis may result from systemic illness (e.g., diabetes mellitus, hyperthyroidism, hypogonadism, chronic renal failure, rheumatoid arthritis, and malignancy) or medications (e.g., corticosteroids, ethanol, tobacco, barbiturates, and heparin). Treatment of secondary osteoporosis generally involves resolution or management of the underlying cause.

There are three types of primary osteoporosis: idiopathic, Type I, and Type II. Idiopathic osteoporosis occurs in children or young adults of both sexes with normal gonadal function. Type I osteoporosis (postmenopausal osteoporosis) is loss of trabecular bone due to estrogen lack at menopause. It occurs between the ages of 51 and 75 years and is more prevalent in women than in men. Vertebral crush fractures are common in Type I osteoporosis. It is generally caused by postmenopausal endocrinologic changes. Type II osteoporosis is loss of cortical and trabecular bone due to long-term remodeling inefficiency, dietary inadequacy, and activation of the parathyroid axis with age. It occurs in those of greater than 70 years, is twice as common in women than in men, and is more gradual and age-related. Type II osteoporosis may be associated with age-related reduction in vitamin D synthesis or resistance to vitamin D activity. In women, Type I and Type II osteoporosis may exist together.

The primary regulators of adult bone mass include physical activity, reproductive endocrine status, and calcium intake. Optimal maintenance of bone requires sufficiency in all three areas, and deficiency in one area cannot be compensated by excessive attention in the other areas. Prevention for osteoporosis calls for regular physical activity, attention to nutritional status in children and elderly with increased dietary calcium and/or vitamin D, and estrogen replacement in menopausal women. Current symptomatic treatment for osteoporosis involves orthopedic support devices, analgesics, heat, massage, and hyperextension exercises.

Pharmacological treatment for osteoporosis involves administration of agents which either decrease the rate of bone resorption and thus slow the rate of bone loss or increase the rate of bone formation. The only drugs approved for use in the United States are those that decrease bone resorption. Antiresorptive drugs include supplemental calcium, vitamin D and its analogs, menopausal estrogen replacement, calcitonin (inhibitor of osteoclastic bone resorption), bisphosphonates (inhibitor of osteoclastic bone resorption), and thiazide diuretics (inhibit urinary Ca++ excretion and constrain bone loss). Bone-forming agents include fluoride, androgens, and parathyroid hormone.

Antiresorptive treatment successfully maintains but does not increase bone mass. Agents that stimulate new bone formation are either problematic or experimental. Consequently, strategies for increasing bone mass in osteoporosis patients remains elusive. Combination therapies involving antiresorptive and bone-forming agents have been used with some success to offset negative side effects of any one agent, but the long-term effects of such treatment is unknown. Therefore, new methods by which bone resorption is decreased and/or bone mass is increased with minimal side effects are desirable.

DETAILED DESCRIPTION

Figure 1A:
FIG. 1A is a digitized representation of a photograph taken prior to ASPARTAME™ (APM) treatment, showing the lateral margin of left tibial plateau and head of fibula in a. p. view.
Figure 1B:
FIG. 1B is a digitized representation of a photograph taken after 1.4 years of APM treatment, showing the lateral margin of left tibial plateau and head of fibula in a. p. view. Increased cortical mineralization and decreased bone resorption at the bone surface are apparent.
Figure 2A:
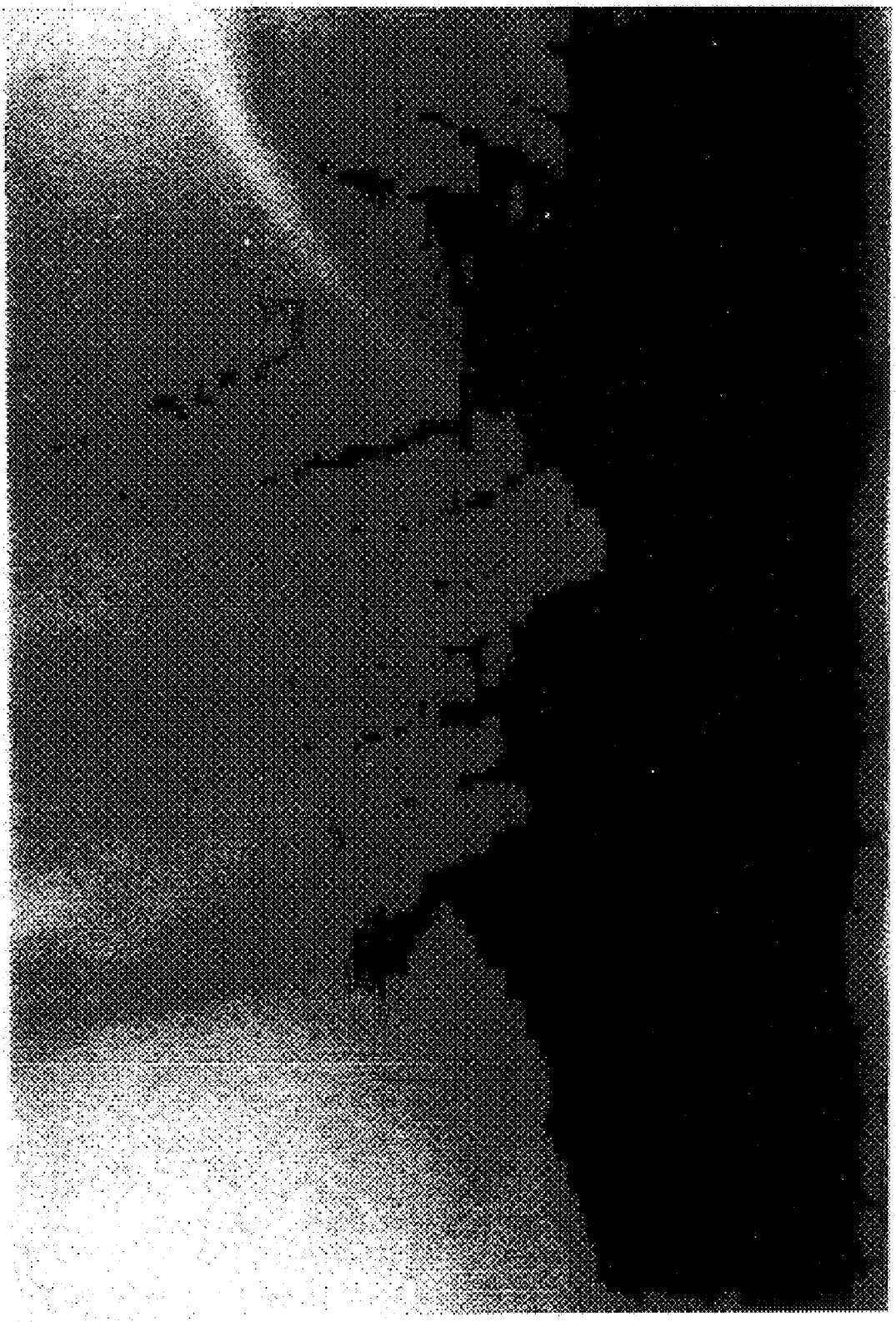
FIGS. 2A and 2B are digitized representations of FIGS. 1A and 1B, respectively, corrected to print maximum X-ray exposure at a similar level of maximal optical density. Increased cortical mineralization and decreased bone resorption at the bone surface are apparent.
Figure 2B:
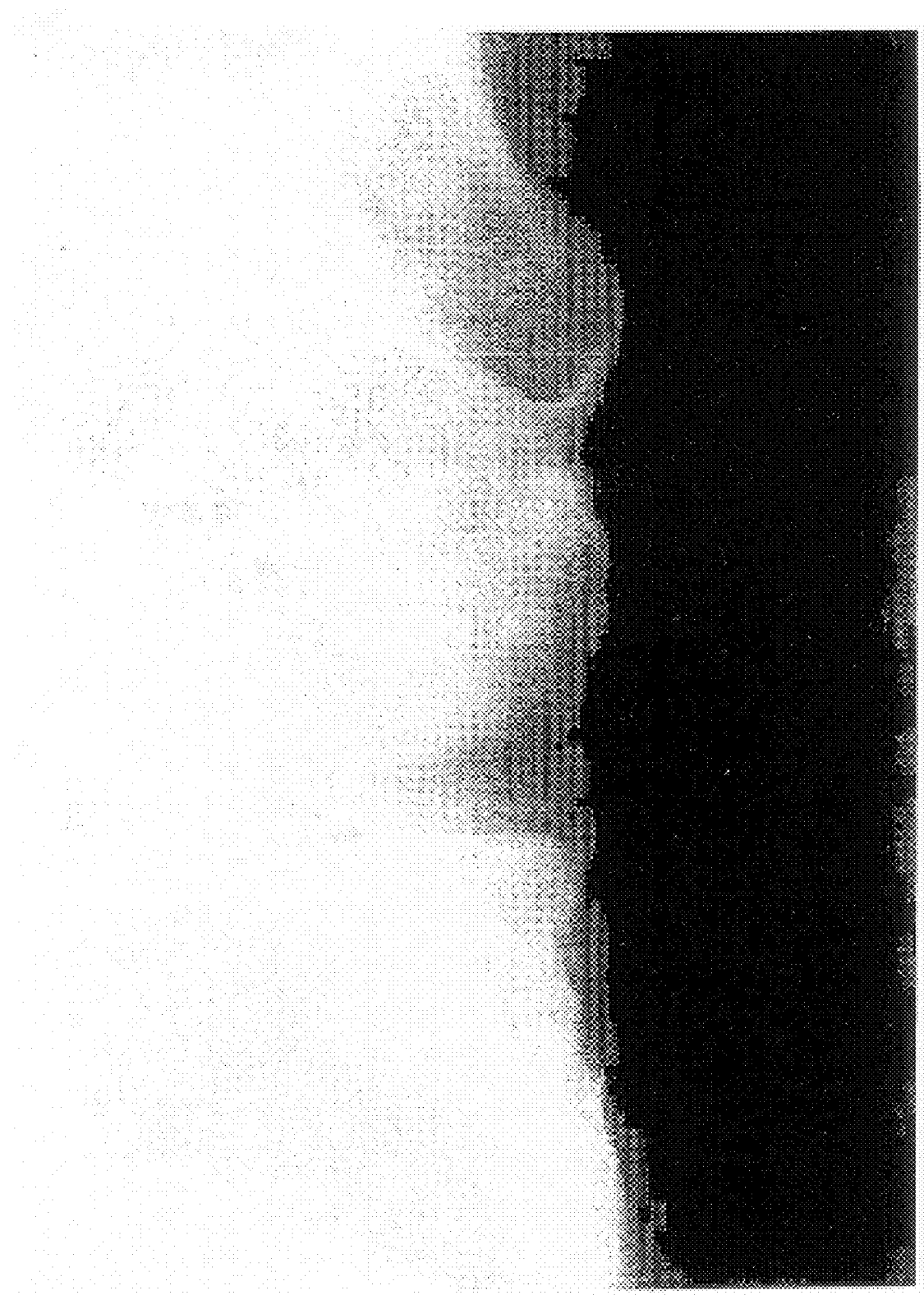
Figure 3A:
FIG. 3A is a digitized representation of a photograph taken prior to APM treatment, showing the superior edge lateral view of the patella.
Figure 3B:
FIG. 3B is a digitized representation of a photograph taken after 1.4 years of APM treatment, showing the superior edge lateral view of the patella. Increased cortical mineralization and decreased bone resorption at the bone surface are apparent.
Figure 4A:
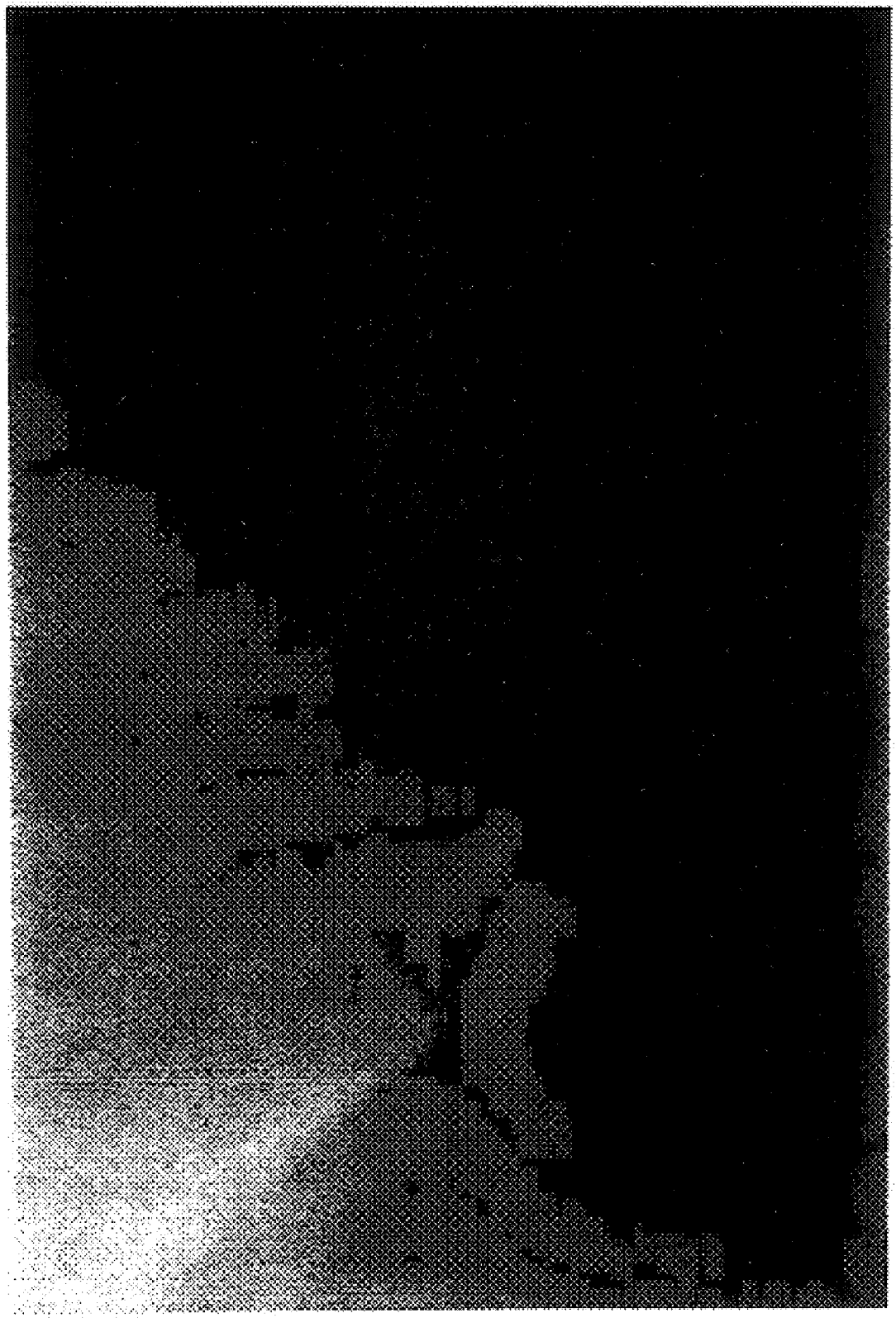
FIG. 4A is a digitized representation of a photograph taken prior to APM treatment, showing the anterior edge of the tibial plateau laterally.
Figure 4B:
FIG. 4B is a digitized representation of a photograph taken after 1.4 years of APM treatment, showing the anterior edge of the tibial plateau laterally. Increased cortical mineralization and decreased bone resorption at the bone surface are apparent.
Figure 5A:
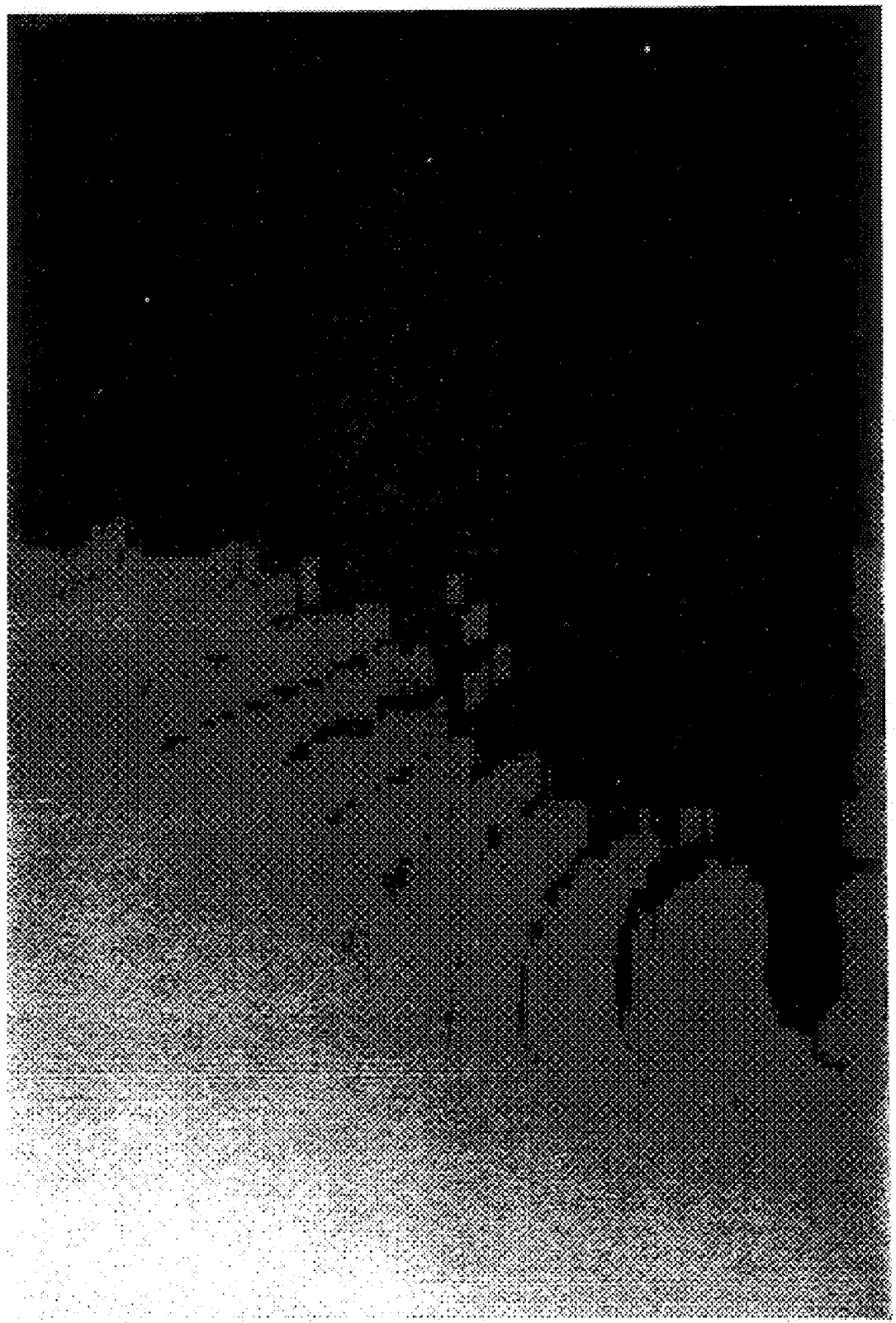
FIG. 5A is a digitized representation of a photograph taken prior to APM treatment, showing the medial edge of the left femur at just above the tibial plateau
Figure 5B:
FIG. 5B is a digitized representation of a photograph taken after 1.4 years of APM treatment, showing the medial edge of the left femur at just above the tibial plateau. Increased cortical mineralization and decreased bone resorption at the bone surface are apparent.

It has now been found that N-L-alpha-aspartyl-L-phenylalanine 1-methyl ester (APM), which has been sold under the trade name of ASPARTAME™ ("APM"; G.D. Searle & Company, Skokie, Ill.) and its derivatives offer medicinal qualities beneficial in the treatment of certain bone diseases, namely, osteoarthritis, osteoporosis, and rheumatoid arthritis. With respect to osteoarthritis and osteoporosis, APM has been found to produce a decrease in bone resorption and an increase in bone mass. APM has been shown to interfere with the effects of TNF-α in the inflammatory process. Particularly, in rheumatoid arthritis, APM has been shown to reduce the pathological arthritic effects of TNF-α and to decrease the progression of rheumatoid arthritis. Further, APM provides antipyretic effects commonly associated with infection, tissue damage and inflammation.

For the treatment of osteoarthritis and osteoporosis, an effective amount of APM which can effect regression of bone resorption is from about 0.75 to about 3 milligrams per kilogram body weight. A preferred range is from about 1.75 to about 2.5 milligrams per kilogram body weight. Most preferred is about 2 milligrams per kilogram body weight. The dosage is repeated over time, preferably at 2 milligrams per kilogram body weight every 8 hours.

For the treatment of rheumatoid arthritis, an effective amount of APM which can effect regression of the disease is from about 1.5 to about 3 milligrams per kilogram body weight. A preferred range is from about 1.75 to about 2.25 milligrams per kilogram body weight. Most preferred is about 2 milligrams per kilogram body weight. The dosage is repeated over time, preferably at 2 milligrams per kilogram body weight every 8 hours.

APM and its derivatives also offer antipyretic action. One can use an effective amount of APM to effect a reduction in fever within three hours of dosage. For a ~70 kilogram adult, an effective amount of APM which can effect fever reduction after one dose is from about 1 milligram per kilogram body weight to about 9 milligrams per kilogram body weight. A preferred range is from about 2 milligrams per kilogram body weight to about 6 milligrams per kilogram body weight. Most preferred is about 3 milligrams per kilogram body weight. The dosage can be repeated over time for continued relief, preferably every six hours.

APM has been previously identified as having analgesic properties (U.S. Pat. No. 5,654,334 issued Aug. 5, 1997, to Edmundson, et al.). It can be administered together with analgesics such as acetaminophen, phenacetin, aspirin, ibuprofen, phenylbutazone, indomethacin and derivatives, opiates and derivatives, piroxacam, and steroidal and non-steroidal anti-inflammatory agents, providing additive analgesic and antipyretic properties as well as treatment of bone diseases.

APM can be administered orally, parenterally, intraperitoneally, or sublingually. It can be administered via ingestion of a food substance containing APM in an amount sufficient to achieve therapeutic levels. Alternatively, it can be enclosed in capsules, compressed into tablets, microencapsulated, entrapped in liposomes, in solution or suspension, alone or in combination with a substrate immobilizing material such as starch or poorly absorbable salts. Pharmaceutically compatible binding agents and/or adjuvant materials can be used as part of a composition. Tablets or capsules can contain any of the following ingredients, or compounds of similar nature: a binder such as microcrystalline cellulose, gum tragacanth or gelatin; an excipient such as starch or lactose, an integrating agent such as alginic acid, corn starch; a lubricant such as magnesium stearate; a glidant such as colloidal silicon dioxide; and additional sweetening and flavoring agents. When a capsule form is used, a liquid carrier such as a fatty oil may be used. Capsules and tablets can be coated with sugar, shellac and other enteric agents as is known. APM can also be in a controlled-release formulation.

APM is available commercially. Its preparation is also disclosed in U.S. Pat. No. 3,492,131. It is believed that various modifications can be made to the APM molecule and the resulting derivatives will also have utility in the claimed invention. Since the 1-methyl ester portion of the molecule is not believed to contribute to the activity of the molecule, N-L-alpha-aspartyl-L-phenylalanine itself or other lower alkyl esters are believed to be effective. Other possible physiologically acceptable derivatives are believed to include N-acyl-L-(beta-substituted)-aspartyl-L-phenylalanine lower alkyl esters and N-acyl-L-(beta-substituted)-aspartyl-L-phenylalanine. Chemical modifications made to the APM molecule which do not reduce the physiologically active properties disclosed herein thus fall within the scope of this invention.

EXAMPLE 1

Regression of Osteoarthritis and Osteoporosis

Prior to treatment, a first set of X-rays were taken of three patients suffering from osteoarthritis. After undergoing APM treatment of 1.5–2.7 mg per kilogram body weight three times a day for 1.4 years, a second set of X-rays were taken and compared to the first set.

In Patient #1 (FIGS. 1A, 1B, 2A, 2B, 3A, 3B, 4A, 4B, 5A and 5B), the second set of X-rays showed that the cortical bone surfaces were altered after treatment, indicating decreased bone resorption and no further apparent disease progression. There was a marked increase in cortical mineralization (deposition of calcium in bone), suggesting enhanced mineralization as an outcome of APM treatment. Patient #1 began walking without a cane and returned to normal activity.

Similar X-ray findings were obtained with Patient #2 and Patient #3. Mineralization effects were again observed. Bone resorption was noted to be decreased but to a lesser extent than that observed for Patient #1.

Patient #2, a patient suffering from osteoarthritis and rheumatoid arthritis, has typical physical deformities of the hands caused by the diseases, including ulnar deviations of carpal bone with subluxations and heberdens nodes. She also has disease in her back and knees. After 0.5 years of treatment with APM, a reduction in synovial swelling, bone thickening, and decreased tenderness in her hands were observed. X-rays taken before and after 1.4 years of treatment suggest increased calcium deposition, changes in the cortical bone that indicated decreased bone reabsorption, and possible evidence of bone remodeling suggestive of normal healing.

EXAMPLE 2

New Dental Bone Formation

A 65 year old male, undergoing APM treatment for two years at 1.75 to 2.2 milligrams per kilogram body weight taken three times a week either before or after exercise, received dental X-rays. When the dental X-rays were compared to X-rays taken two years prior, the new X-rays clearly indicated the laying down of new bone. The unusual occurrence of laying down new bone in a 65 year old male was attributed to the APM treatment.

EXAMPLE 3

Regression of Bone Spur

A fifty-four year old male patient was unable to walk due to foot pain in the metatarsal area of his right foot during an overseas trip. The subdural region covering the entire metatarsal set of bones was filled with blood, and within two hours of onset, walking was impossible. Upon examination by a physician, orthotic shoes designed for osteoarthritis were recommended. Residual pain and tenderness upon walking remained for one more month. After six months, additional orthotic inserts were prescribed and normal athletic routine was resumed.

After three years, pain resumed upon extensive walking. Examination of the right foot by a physician revealed two pustulant and open ulcers which over a period of three days without treatment became gangrenous. On the fourth day, an orthopedic physician cleaned and dressed the wounds, and directed the patient to physical therapy. More elaborate orthotic devices and shoes were designed to take weight off the foot, and acute symptoms gradually disappeared over a period of the next six months.

Twelve years after the first episode, the patient continued use of the orthotic inserts but discontinued use of the orthotic shoes. He began APM treatment at 2.25 milligrams per kilogram body weight consumed over a 15 minute period three times a week. One year later, the patient tore the fascia on the arch of the right foot. Upon examination of X-rays of the right foot, the orthopedic surgeon concluded that the metatarsals appeared radiologically normal in every respect with no signs of spicules. No further evidence of ulceration or internal bleeding in this region was observed even after strenuous exercise. The apparent termination of the arthritic process was attributed to the APM treatment.

EXAMPLE 4

Regression of Joint Swelling and Tenderness in Finger

A 63 year old male was experiencing pain and swelling of the metacarpal interphalangeal (MIP) joint of his left middle finger. He was medicated with 2.1 milligrams per kilogram body weight APM, and within one hour, the MIP joint measured 62 mm, appeared reddened and inflamed, and was painful to the touch. At two hours post-treatment, the MIP joint measured 62 mm and remained tender to touch but pain in general had decreased. At three hours post-treatment, the MIP joint measured 60 mm, was less tender, and the patient was able to touch it without experiencing pain. The redness had disappeared in eight hours.

EXAMPLE 5

TNF Antagonism

APM was evaluated for its capacity to block the development of rheumatoid arthritis by antagonizing TNF-α.

For this study, TNF-α transgenic mice (Taconic, Germantown, N.Y.) were utilized. These mice carry a 3' modified human TNF transgene, exhibiting deregulated TNF expression and progressive development of severe inflammatory arthritis without experimental induction. The arthritic condition appears in 100% of these mice at a consistent time of onset, with visible swelling of ankle joints at 6–8 weeks, synovial hyperplasia and accumulation of inflammatory infiltrates at 9 weeks, and distortion of digits of fore and hind paws at 12–14 weeks.

Four week old TNF-α mice weighing approximately 21 grams were divided into control and treatment groups. APM was administered orally to the treatment group by coating food with powdered APM obtained from Sigma Chemical Co. (St. Louis, Mo.) at four grams of APM per 1000 grams of food. Weight change and food and drug consumption were observed every other day. Each mouse ate 4–5 grams of food daily, resulting in a dosage of 19–22 milligrams of APM per day. Table I indicates the weight gain in control and treatment mice. Both groups experienced similar weight gains of 3–5 grams.

TABLE I

Weight Gain in Mice

| Mouse | Treatment Type | Total Weight Gain (g) |
|---|---|---|
| 1 | APM | 2.60 |
| 2 | APM | 4.10 |
| 3 | APM | 4.30 |
| 4 | APM | 3.20 |
| 5 | APM | 2.80 |
| Average Weight | APM | 3.40 |
| 6 | Control | 5.70 |

TABLE I-continued

Weight Gain in Mice

| Mouse | Treatment Type | Total Weight Gain (g) |
|---|---|---|
| 7 | Control | 4.50 |
| 8 | Control | 4.10 |
| 9 | Control | 4.80 |
| Average Weight | Control | 4.78 |

Data was collected three times at three week intervals to compare the disease progress of the control and treated mice. Photographic documentation and plaster impressions were used to create images and imprints of both front and rear paws for each mouse before treatment, and subsequently to record any change in joint size.

To make plaster impressions, a direct pressure impression was made of each paw using a modeling substance such as PLAY-DOH®, while restraining the animal. Plaster was then poured into the impression and allowed to harden. After peeling off the modeling substance, the plaster impression was marked with an identifying mark, dated, and photographed. The is photograph of the impression was calibrated to the casting, and relevant dimensions of the digital width and carpal width were measured on the photograph.

Figure 6:
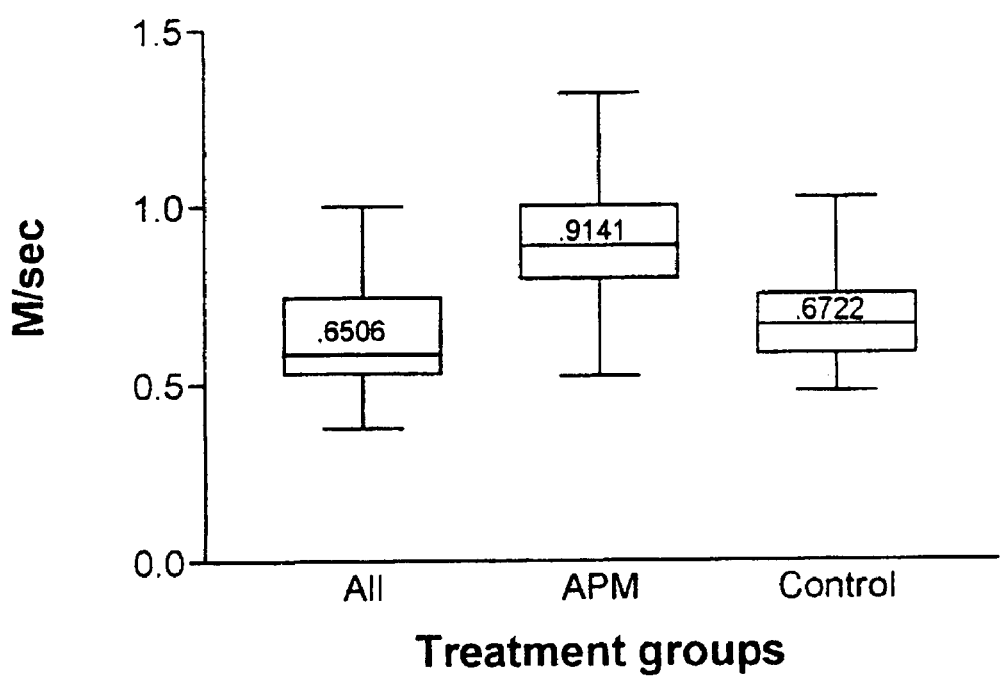
FIG. 6 is a graph depicting running speed for TNF-α transgenic mice with and without treatment with APM at Week 6 compared to all mice at Time 0.
Figure 7:
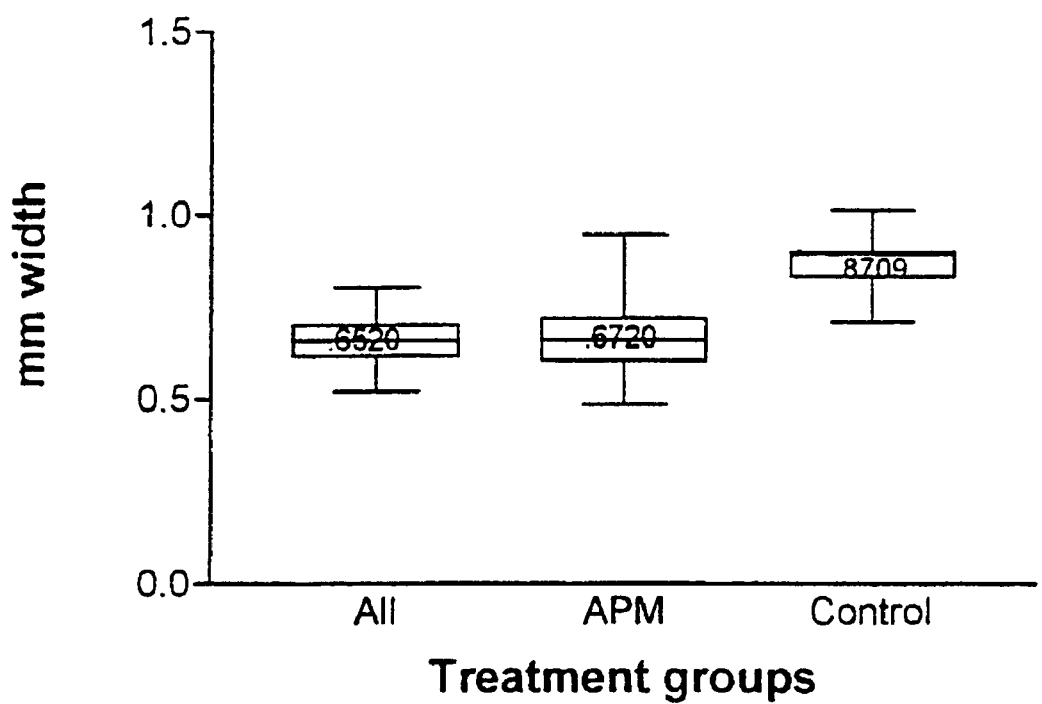
FIG. 7 is a graph depicting plaster digit widths for TNF-α transgenic mice with and without treatment with APM at Week 6 compared to all mice at Time 0.

The results from these measurements are given in FIGS. 6 and 7 for plaster digit widths and carpal widths, respectively. FIG. 6 compares digit widths for all mice at Week 0, treated mice at Week 6 and control mice at Week 6. All mice at Week 0 vs. control mice at Week 6 and treated mice vs. control mice at Week 6 are statistically significant with $P<0.001$. Joint size in the treated mice at Week 6 is similar to joint size for all mice at Week 0. Treatment with APM has retarded the digit swelling in the mice.

For plaster carpal widths, FIG. 7 shows differences in carpal widths for all mice at Week 0, treated mice at Week 6 and control mice at Week 6. The mean for the treated mice at Week 6 is significantly different from the mean for all mice at Week 0 and the mean for control mice at Week 6 ($P<0.001$). The APM treatment has decreased swelling and impacted the disease process in the mice. The large range of values in all the mice at Week 0 may possibly be due to the fact that front and back paws were not distinguished and the fact that front paws are smaller than back paws could have biased that part of the data.

Figure 8:
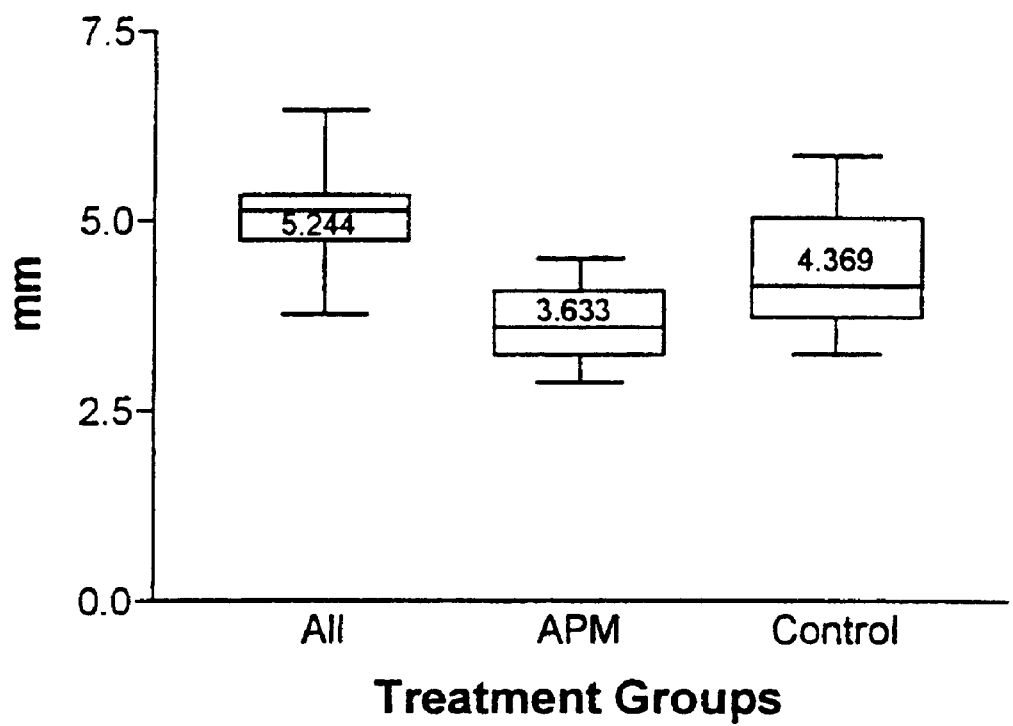
FIG. 8 is a graph depicting plaster carpal widths for TNF-α transgenic mice with and without treatment with APM compared to all mice at Time 0.
Figure 9A:
FIG. 9A and FIG. 9B are digitized representations of photographs comparing plaster impressions of TNF-α transgenic mice with and without treatment with APM, respectively.
Figure 9B:
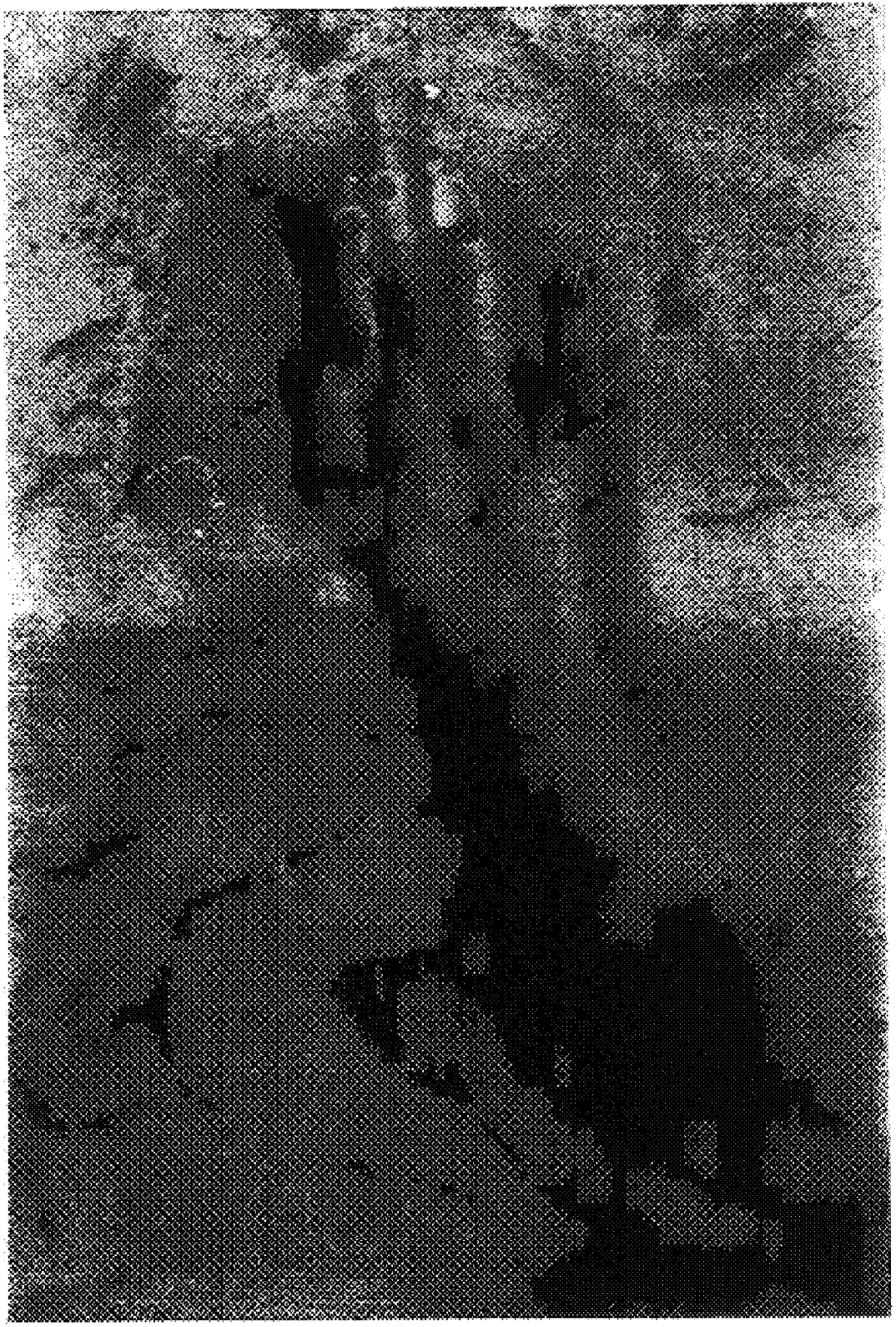
Figure 10A:
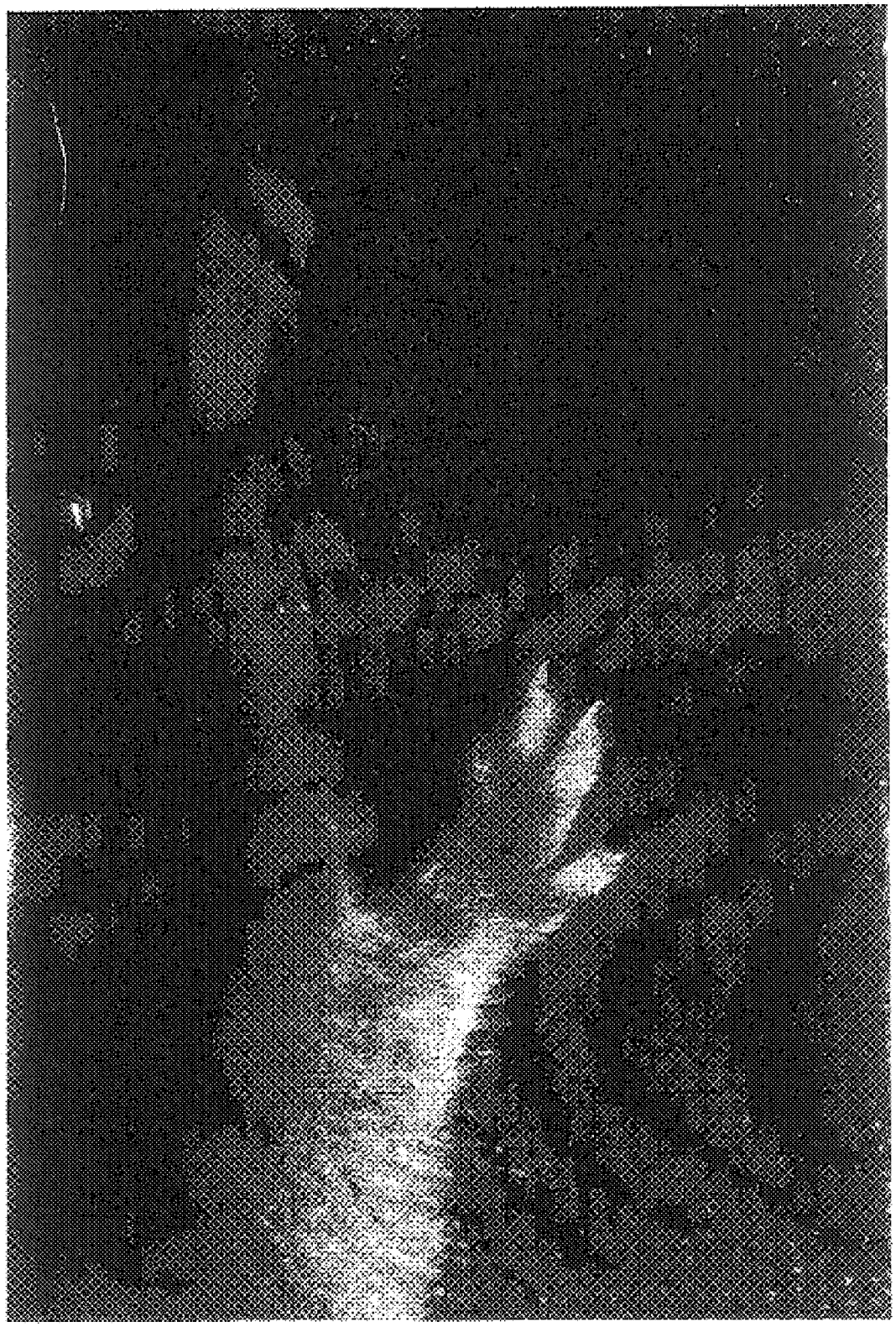
FIG. 10A and FIG. 10B are digitized representations of photographs comparing TNF-α transgenic mice with and without treatment with APM, respectively.
Figure 10B:
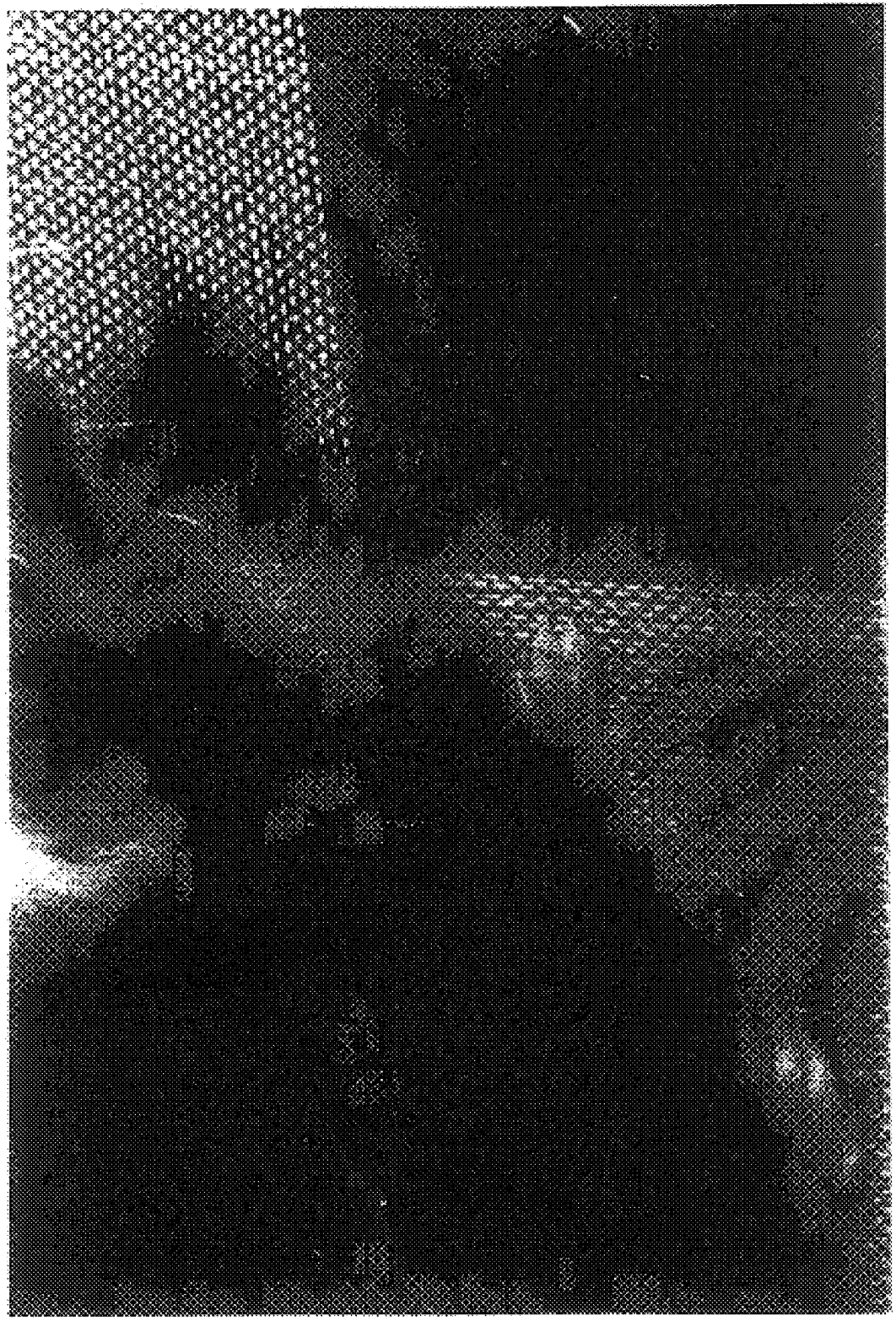

A comparison of plaster impressions from a treated mouse and a control mouse at Week 6 is given in FIG. 8. The treated paw is less swollen in the digits and in the lower paw. The digits in the control mouse are displaced upward, while the digits in the treated paw come straight out with no appearance of a shelf. The beginning of subluxation is visible in the control mouse paw.

High speed photographs were also taken of each paw using a 100 mm Macro lens and an electronic flash at 1/2000 sec shutter speed. Each mouse cage was given a backdrop with a plaid material using a different patterned fabric for the control mice and treated mice. The patterned fabric then served as a size and color calibration grid. The photographs were digitally scanned and computer enlargements were produced. The patterned fabric grid and paw measurements on the computer enlargements were measured in millimeters and recorded. Again, using proportional adjustments between the patterned fabric grid of the computer enlargement and the actual cloth, the actual dimensions of the digital width and carpal width were determined. To ensure measurements were accurate, the plaster impression and high-speed photography techniques were utilized independently and results compared. There was good correlation between the two data sets, producing a straight line with a slope of $1.165\pm0.024$ and a goodness of fit at 94.7%. It also supported the position that combining front and back paw carpal measurements accounts for the wide range of values in all the mice at Week 0.

Photographs of a treated mouse and a control mouse at Week 6 are given in FIG. 9A, FIG. 9B, FIG. 10A and FIG. 10B. The treated mouse has a natural spread of the digits and a natural bend of the foreleg which are absent in the control mouse. The control animal's apparent inability or unwillingness to spread its paw suggests effects from swelling that can be seen. The swelling obscures the detail that is present in the treated paw.

Loss of function for each mouse was measured as changes in running speed, recorded using video documentation. Each mouse was video-recorded for five minutes on three occasions. During the recording, the mouse was induced to run by lightly tapping the mouse if necessary. The plaid material backdrop on the mouse cage provided a grid from which to determine the starting and stopping points of each run. Raw data measurements were taken of the distance run and the number of video frames required to record that distance. Using the recording speed of the video camera (30 frames per second), the raw data measurements were then converted to precise running speed in meters per second.

Figure 11A:
FIG. 11A and FIG. 11B are digitized representations of photographs comparing TNF-α transgenic mice with and without treatment with APM, respectively.
Figure 11B:

FIG. 11A and FIG. 11B, respectively, show the mean running speed results for the treated and control groups. The graph compares the running speeds of all the mice at Week 0, treated mice at Week 6, and control mice at Week 6. The mean running speed for all mice at Week 0 vs. the mean running speed for treated mice at Week 6 is statistically significant with $P<0.001$. The mean running speed for control mice at Week 6 is not significantly different from the mean running speed for all mice at Week 0. This indicates that the treated mice ran faster than the control mice at Week 6.

In analyzing the actual videos, a loss of function in some of the control mice was apparent and the control mice seemed less active than the treated mice. Differences between the treated and control group included: (1) the control mice responded less to touch than the treated group; (2) it was more difficult to get the control group to run the length of the cage than the treated group; and (3) the control group showed a change in running style (moving in a hopping motion, lifting their hind quarters in the air to avoid putting weight on their feet) while the treated group did not.

Figure 12A:
FIG. 12A and FIG. 12B are digitized representations of infrared photographs comparing TNF-α transgenic mice with and without treatment with APM, respectively.
Figure 12B:

Infrared color film and a night vision scope were used to document redness and/or heat in the joints and to observe circulation. FIG. 12A and FIG. 12B, respectively, show a comparison of a treated mouse's front paw and a control mouse's front paw at Week 6. The treated mouse has brighter feet and ears than the control mouse. This suggests that the control mouse is suffering from poor circulation, possibly vasculitis which would accompany a severe arthritis.

The data analysis of this study indicated that APM reduces the pathological effects of TNF-α over-expression in these transgenic mice and also the progression of the disease arthritis. Treated mice experienced less loss of function, less joint swelling, and possibly had better circulation than the control mice. Since these transgenic mice have been accepted as an animal model for studying target anti-TNF-α and other agents for the treatment of rheumatoid arthritis, these studies indicate that APM is effective in reducing the deleterious effects of TNF-α and also the progression of the rheumatoid arthritis.

EXAMPLE 6

Antipyretic Effects of APM in Rats

Using the technique described by Father, et al., *Am J Physiology* 267:R1431–1436 (1994), an unblinded study was begun with twenty rats to measure the antipyretic effects of APM. Two rats suffered gavage deaths, leaving a total of eighteen rats to complete the study.

Using four rats at one time, the rats were restrained, and anesthesia was administered by pentobarbital injection and maintained throughout the experiment by subsequent injections. Body temperature for each rat was measured rectally using a thermocouple. The anesthetized rats tended to become hypothermic upon administration of the anesthesia, and heating pads were used to correct for anesthesia effects, with two rats from differing treatment groups per heating pad. After establishing a baseline temperature reading, two rats were gavaged with aqueous APM (200 milligrams) and two were gavaged with normal saline. After fifteen minutes, one rat gavaged with aqueous APM and one rat gavaged with normal saline received an intramuscular (IM) injection in the left lower limb of 0.3 ml turpentine (100%). Likewise, one rat gavaged with aqueous APM and one rat gavaged with normal saline received an intramuscular (IM) injection in the left lower limb of 0.3 ml normal saline. Body temperature measurements were obtained at 10, 15, 30, 45, 60, 90, 120, 150, 180, 210, 240, 270, 300, 330, and 360 minutes post IM injection.

The experiment was repeated five times with different rats. The results are given in Tables II–V, and the mean temperature readings for each of the four treatment groups is given in Table VI and illustrated in FIG. 13 as a graph depicting the average temperature of rats following the IM administration of turpentine or saline and subsequent administration of APM or saline. The results indicate the APM was capable of reducing fever when administered prophylactically.

Figure 13:
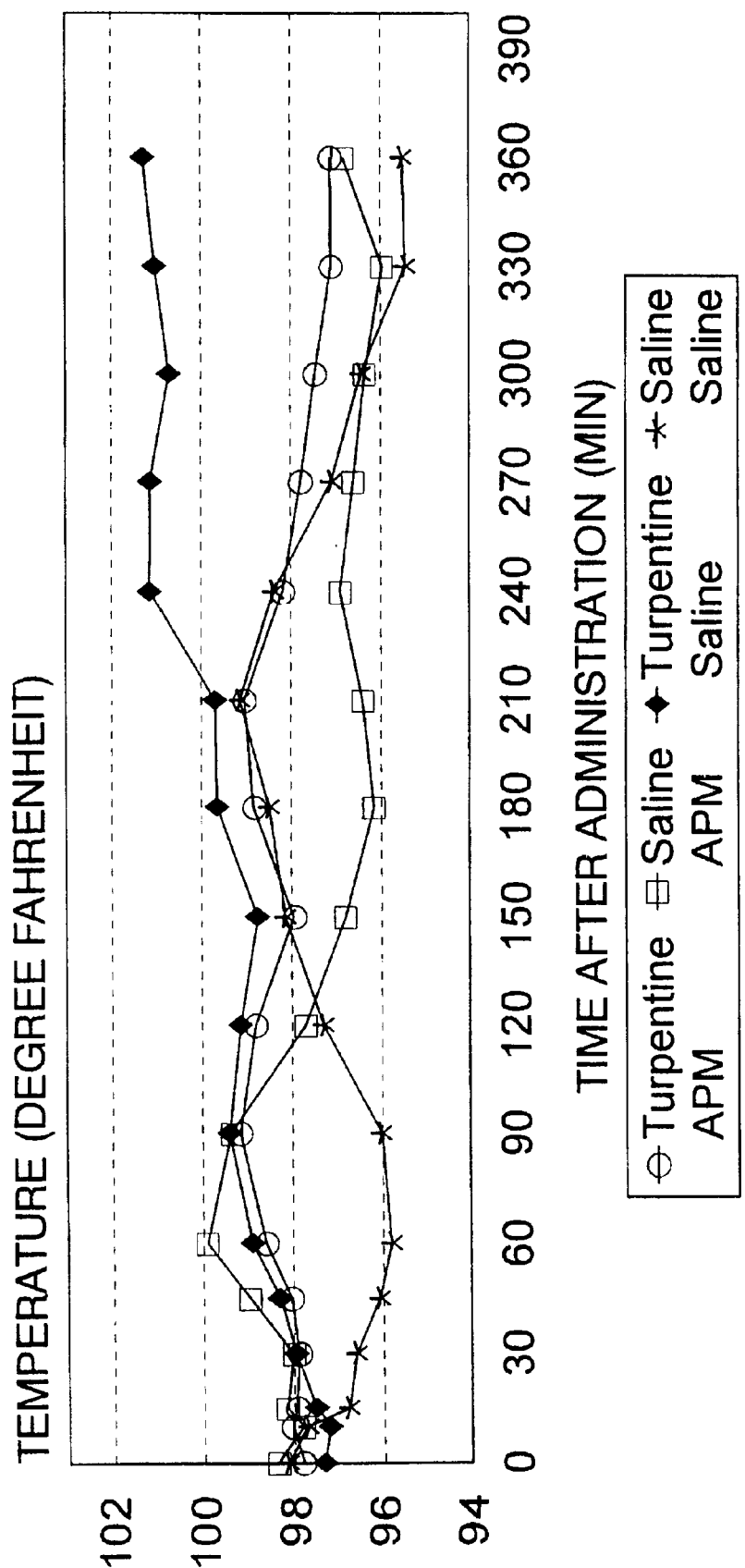
FIG. 13 is a graph depicting the average temperature of rats following the IM administration of turpentine or saline and subsequent administration of APM or saline.

As shown in FIG. 13, the average body temperature in the saline-gavaged/turpentine-treated rats increased over time, especially after 210 minutes post-turpentine treatment. By comparison, the APM-gavaged/turpentine-treated rats more closely mimicked the normal body temperature of the saline-gavaged/saline-treated control rats after 150 minutes.

The APM blocked the inflammatory responses which typically occur after IM turpentine injection. Using this standard, well established model for identifying a febrile response, APM appears to have an effect in reducing fever.

TABLE II

Body Temperature After APM/Turpentine Treatment

| Time | Rat #1 | Rat #2 | Rat #3 | Rat #4 | Rat #5 |
|---|---|---|---|---|---|
| 0 min. | 97.8 | 98.5 | 97.7 | 98.2 | 96.8 |
| 10 min. | 98.6 | 98.8 | 98.2 | 98.2 | 96.4 |
| 15 min. | 98.2 | 98.4 | 98.8 | 96.7 | 97.6 |
| 30 min. | 98.9 | 98.5 | 98.1 | 97.4 | 96.5 |
| 45 min. | 100.1 | 98.3 | 98.2 | 96.8 | 98.6 |
| 60 min. | 99.9 | 97.5 | 98.8 | 97.1 | 99.6 |
| 90 min. | 99.8 | 97.4 | 99.8 | 99.1 | 99.6 |
| 120 min. | 96.6 | 100.1 | 99.3 | 99.2 | 98.8 |

TABLE II-continued

Body Temperature After APM/Turpentine Treatment

| Time | Rat #1 | Rat #2 | Rat #3 | Rat #4 | Rat #5 |
|---|---|---|---|---|---|
| 150 min. | 96 | 98.7 | 98.4 | 99 | 97.6 |
| 180 min. | 97.8 | 98 | 99.4 | 100.9 | 98 |
| 210 min. | 99.5 | 97.1 | 99.1 | 99.9 | 99.5 |
| 240 min. | 100.3 | 96.5 | 98.7 | 98.9 | 96.5 |
| 270 min. | 98.4 | 96.4 | 99.4 | 98.2 | 96.5 |
| 300 min. | 97.7 | 96.4 | 99.5 | 97.1 | 96.6 |
| 330 min. | 97.7 | 95.4 | 99.2 | 96.6 | 96.6 |
| 360 min. | 97.7 | 96.36 | 98.9 | 96.2 | 96.4 |

TABLE III

Body Temperature After APM/Saline Treatment

| Time | Rat #1 | Rat #2 | Rat #3 | Rat #4 |
|---|---|---|---|---|
| 0 min. | 98.1 | 98.6 | 99.1 | 98.2 |
| 10 min. | 96.8 | 98.8 | 98.6 | 98.1 |
| 15 min. | 96.7 | 99.6 | 98.4 | 99.1 |
| 30 min. | 96.9 | 99.1 | 98.7 | 98.3 |
| 45 min. | 98.3 | 99.6 | 98.7 | 98.4 |
| 60 min. | 99.8 | 100 | 99.1 | 98.9 |
| 90 min. | 98.9 | 99.8 | 100.2 | 100.2 |
| 120 min. | 96.8 | 98.6 | 99 | 99.2 |
| 150 min. | 96.9 | 96.7 | 97.6 | 99.1 |
| 180 min. | 95.5 | 96.8 | 96 | 97.7 |
| 210 min. | 95.9 | 96.9 | 95 | 98.6 |
| 240 min. | 97.5 | 96.3 | 94.8 | 99.1 |
| 270 min. | 96.7 | 96.5 | 94.3 | 100.7 |
| 300 min. | 95.9 | 96.8 | 94.1 | 100.5 |
| 330 min. | 94.8 | 97.1 | 94 | 100.2 |
| 360 min. | 95 | 98.08 | 94.44 | 99.8 |

TABLE IV

Body Temperature After Saline/Turpentine Treatment

| Time | Rat #1 | Rat #2 | Rat #3 | Rat #4 | Rat #5 |
|---|---|---|---|---|---|
| 0 min. | 95.4 | 96.5 | 98.9 | 98.6 | 97.2 |
| 10 min. | 96.2 | 96.9 | 97.9 | 98.1 | 96.9 |
| 15 min. | 96.3 | 98.4 | 100.1 | 96.4 | 96.3 |
| 30 min. | 95.8 | 100.4 | 100.3 | 97 | 96.2 |
| 45 min. | 96.2 | 101.1 | 100.4 | 98.2 | 95.5 |
| 60 min. | 96.5 | 101.3 | 100.6 | 99.4 | 96.6 |
| 90 min. | 95.3 | 102.1 | 100.4 | 101.5 | 97.6 |
| 120 min. | 94.6 | 102.5 | 100.4 | 100.6 | 97.5 |
| 150 min. | 94.7 | 102.3 | 100.2 | 100.2 | 96.3 |
| 180 min. | 95.2 | 102.1 | 100.3 | 102.8 | 97.8 |
| 210 min. | 95.4 | 101.2 | 100.4 | 103.7 | 97.7 |
| 240 min. | 95.5 | 100.9 | 106.6 | 102.9 | 99.8 |
| 270 min. | 99.2 | 99.6 | 101.1 | 101.7 | 104 |
| 300 min. | 99 | 98.8 | 101.1 | 99.9 | 104.7 |
| 330 min. | 101.2 | 98.3 | 101.5 | 98.8 | 105.3 |
| 360 min. | 102.1 | 98.9 | 101.6 | 98.4 | 105.4 |

TABLE V

Body Temperature After Saline/Saline Treatment

| Time | Rat #1 | Rat #2 | Rat #3 | Rat #4 |
|---|---|---|---|---|
| 0 min. | 98.3 | 97.6 | 97.6 | 99 |
| 10 min. | 98.1 | 97.4 | 97.6 | 98.9 |
| 15 min. | 98.3 | 96.7 | 95.3 | 98.9 |
| 30 min. | 98.4 | 95.9 | 95.5 | 93.3 |
| 45 min. | 98.1 | 95.4 | 94.7 | 92.3 |

TABLE V-continued

Body Temperature After Saline/Saline Treatment

| Time | Rat #1 | Rat #2 | Rat #3 | Rat #4 |
|---|---|---|---|---|
| 60 min. | 98 | 94.9 | 94.5 | 92.5 |
| 90 min. | 97.8 | 95.3 | 94.9 | 95.6 |
| 120 min. | 98 | 97.4 | 96.5 | 96.3 |
| 150 min. | 97.3 | 100.3 | 96.8 | 96.1 |
| 180 min. | 97.2 | 101.4 | 96.8 | 95.1 |
| 210 min. | 99.3 | 101.5 | 96.6 | 96.1 |
| 240 min. | 98.5 | 99.7 | 96.9 | 95.5 |
| 270 min. | 96.5 | 97.7 | 97.1 | 96.1 |
| 300 min. | 95.2 | 96.6 | 97.5 | 97.7 |
| 330 min. | 93.3 | 95.4 | 97.6 | 98.1 |
| 360 min. | 93.5 | 97.35 | 97.6 | 96.1 |

TABLE VI

Average Body Temperature by Treatment Group

| Time | APM Turpentine | APM Saline | Saline Turpentine | Saline Saline |
|---|---|---|---|---|
| 0 min. | 97.80 | 98.35 | 97.32 | 98.13 |
| 10 min. | 98.04 | 97.80 | 97.20 | 97.70 |
| 15 min. | 97.94 | 98.15 | 97.50 | 96.77 |
| 30 min. | 97.88 | 98.00 | 97.94 | 96.60 |
| 45 min. | 98.40 | 98.95 | 98.28 | 96.07 |
| 60 min. | 98.58 | 99.90 | 98.88 | 95.80 |
| 90 min. | 99.14 | 99.35 | 99.38 | 96.00 |
| 120 min. | 98.80 | 97.70 | 99.12 | 97.30 |
| 150 min. | 97.94 | 96.80 | 98.74 | 98.13 |
| 180 min. | 98.82 | 96.15 | 99.64 | 98.47 |
| 210 min. | 99.02 | 96.40 | 99.68 | 99.13 |
| 240 min. | 98.18 | 96.90 | 101.14 | 98.37 |
| 270 min. | 97.78 | 96.60 | 101.12 | 97.10 |
| 300 min. | 97.46 | 96.35 | 100.70 | 96.43 |
| 330 min. | 97.10 | 95.95 | 101.02 | 95.43 |
| 360 min. | 97.112 | 96.83 | 101.28 | 95.50 |

We claim:

1. A method for treatment of a disease effected by TNF-α in a patient comprising administering in a treatment regimen to said patient an effective amount of a compound comprising:

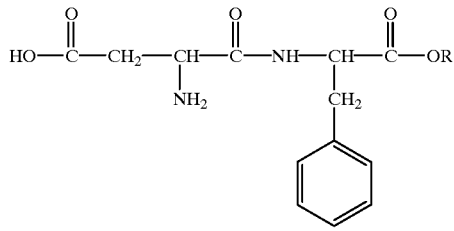

where R is H or an alkyl containing 1 to 6 carbons, wherein said treatment regimen is capable of inhibiting TNF-α activity over time.

2. The method of claim 1, wherein said effective amount of said compound is from about 1.5 milligrams per kilogram body weight to about 3 milligrams per kilogram body weight.

3. The method of claim 1, wherein said effective amount of said compound is from about 1.75 milligrams per kilogram body weight to about 2.25 milligrams per kilogram body weight.

4. The method of claim 1, wherein said effective amount of said compound is about 2 milligrams per kilogram body weight.

5. The method of claim 1, wherein said treatment regimen is administered periodically over one to six months.

6. The method of claim 1, wherein said treatment regimen is administered periodically for at least twelve months.

7. A method for treatment of osteoarthritis in a patient comprising administering in a treatment regimen to said patient an effective amount of a compound comprising:

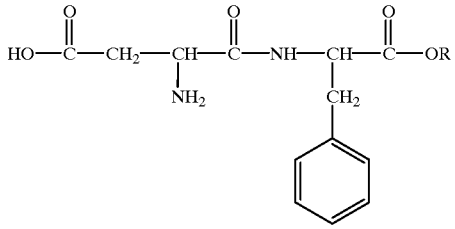

where R is H or an alkyl containing 1 to 6 carbons, wherein said treatment regimen is capable of eliciting decreased bone resorption and increased bone density over time.

8. The method of claim 7, wherein said effective amount of said compound is from about 0.75 milligrams per kilogram body weight to about 3 milligrams per kilogram body weight.

9. The method of claim 7, wherein said effective amount of said compound is from about 1.75 milligrams per kilogram body weight to about 2.5 milligrams per kilogram body weight.

10. The method of claim 7, wherein said effective amount of said compound is about 2 milligrams per kilogram body weight.

11. The method of claim 7, wherein said treatment regimen is administered periodically over one to six months.

12. The method of claim 7, wherein said treatment regimen is administered periodically for at least twelve months.

13. A method for treatment of osteoporosis in a patient comprising administering in a treatment regimen to said patient an effective amount of a compound comprising:

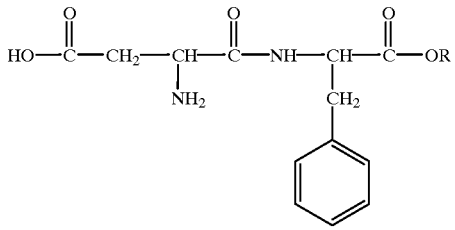

where R is H or an alkyl containing 1 to 6 carbons, wherein said treatment regimen is capable of eliciting decreased bone resorption and increased bone density over time.

14. The method of claim 13, wherein said effective amount of said compound is from about 0.75 milligrams per kilogram body weight to about 3 milligrams per kilogram body weight.

15. The method of claim 13, wherein said effective amount of said compound is from about 1.75 milligrams per kilogram body weight to about 2.5 milligrams per kilogram body weight.

16. The method of claim 13, wherein said effective amount of said compound is about 2 milligrams per kilogram body weight.

17. The method of claim 13, wherein said treatment regimen is administered periodically over one to six months.

18. The method of claim 13, wherein said treatment regimen is administered periodically for at least twelve months.

19. A method for treatment of rheumatoid arthritis in a patient comprising administering in a treatment regimen to said patient an effective amount of a compound comprising:

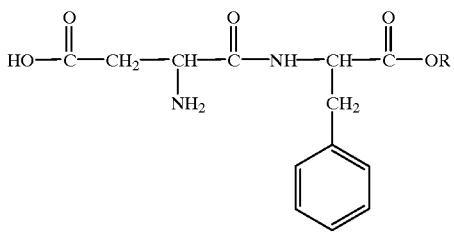

where R is H or an alkyl containing 1 to 6 carbons, wherein said treatment regimen is capable of inhibiting TNF-α activity over time.

20. The method of claim 19, wherein said effective amount of said compound is from about 1.5 milligrams per kilogram body weight to about 3 milligrams per kilogram body weight.

21. The method of claim 19, wherein said effective amount of said compound is from about 1.75 milligrams per kilogram body weight to about 2.25 milligrams per kilogram body weight.

22. The method of claim 19, wherein said effective amount of said compound is about 2 milligrams per kilogram body weight.

23. The method of claim 19, wherein said treatment regimen is administered periodically over one to six months.

24. The method of claim 19, wherein said treatment regimen is administered periodically for at least twelve months.

25. A method for reducing fever in a patient comprising administering prophylactically to said patient an effective amount of a compound comprising:

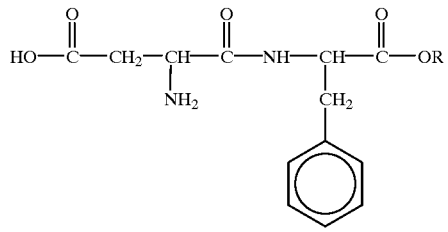

where R is H or an alkyl containing 1 to 6 carbons to affect a reduction in fever in said patient.

26. The method of claim 25, wherein said effective amount of said compound is from about 1 milligram per kilogram body weight to about 9 milligrams per kilogram body weight.

27. The method of claim 25, wherein said effective amount of said compound is from about 2 milligrams per kilogram body weight to about 6 milligrams per kilogram body weight.

28. The method of claim 25, wherein said effective amount of said compound is about 3 milligrams per kilogram body weight.

* * * * *